(12) United States Patent
Hontsu et al.

(10) Patent No.: US 9,205,030 B2
(45) Date of Patent: Dec. 8, 2015

(54) HARD TISSUE REGENERATION MATERIAL AND HARD TISSUE REGENERATION METHOD

(71) Applicant: KINKI UNIVERSITY, Osaka (JP)

(72) Inventors: Shigeki Hontsu, Osaka (JP); Hiroaki Nishikawa, Osaka (JP); Masanobu Kusunoki, Osaka (JP); Kazushi Yoshikawa, Osaka (JP); Kazuyo Yamamoto, Osaka (JP)

(73) Assignee: KINKI UNIVERSITY, Osaka (JP)

( * ) Notice: Subject to any disclaimer, the term of this patent is extended or adjusted under 35 U.S.C. 154(b) by 0 days.

(21) Appl. No.: 13/752,633

(22) Filed: Jan. 29, 2013

(65) Prior Publication Data

US 2013/0236856 A1 Sep. 12, 2013

Related U.S. Application Data (63) Continuation of application No. PCT/JP2011/066955, filed on Jul. 26, 2011.

(30) Foreign Application Priority Data

Jul. 30, 2010 (JP) .................................. 2010-171358

(51) Int. Cl.
  *B32B 9/00* (2006.01)
  *A61K 6/02* (2006.01)
  (Continued)

(52) U.S. Cl.
  CPC ................ *A61K 6/0205* (2013.01); *A61C 5/04* (2013.01); *A61C 19/063* (2013.01); *A61K 6/033* (2013.01);
  (Continued)

(58) Field of Classification Search
  None
  See application file for complete search history.

(56) References Cited

U.S. PATENT DOCUMENTS 4,613,577 A * 9/1986 Tagai et al. ..................... 501/35
5,242,706 A * 9/1993 Cotell et al. ................ 427/2.27
(Continued)

FOREIGN PATENT DOCUMENTS

| JP | 6-319794 | 11/1994 |
|----|----------|---------|
| JP | 2009-61109 | 3/2009 |
| WO | 2007/108373 | 9/2007 |

OTHER PUBLICATIONS

Yan et al. "Characterization of chemical inhomogeneity in plasma-sprayed hydroxyapatite coatings", 2003, Biomaterials, vol. 24, pp. 2585-2592.*

(Continued)

*Primary Examiner* — Humera Sheikh
*Assistant Examiner* — Seth Dumbris
(74) *Attorney, Agent, or Firm* — Wenderoth, Lind & Ponack, L.L.P.

(57) ABSTRACT

Provided are a hard tissue restoration material, which is excellent in hard tissue restoration ability, extremely effective in promoting recalcification of dental enamel, and excellent in protection properties and aesthetic properties, and a hard tissue restoration method. The hard tissue restoration material according to the present invention is a biocompatible ceramic film with flexibility and pliability that is obtained, for example, by immersing a substrate, having the biocompatible ceramic film formed thereon, in a solvent, which does not dissolve the biocompatible ceramic but dissolves at least a portion of the substrate, to dissolve or separate the substrate. Also, with the hard tissue restoration method according to the present invention, the hard tissue restoration material according to the present invention is bonded to or wound around a hard tissue defect site.

11 Claims, 9 Drawing Sheets

(51) Int. Cl.
  *A61K 6/033* (2006.01)
  *A61K 6/06* (2006.01)
  *A61L 27/12* (2006.01)
  *A61C 5/04* (2006.01)
  *A61C 19/06* (2006.01)
  *A61Q 11/00* (2006.01)

(52) U.S. Cl.
  CPC ............... *A61K 6/0643* (2013.01); *A61L 27/12* (2013.01); *A61Q 11/00* (2013.01); *A61L 2430/02* (2013.01); *A61L 2430/12* (2013.01)

(56) References Cited

U.S. PATENT DOCUMENTS

| | | | |
|---|---|---|---|
| 5,543,209 A * | 8/1996 | Duquet et al. | 428/212 |
| 5,676,699 A | 10/1997 | Gogolewski et al. | |
| 2006/0210494 A1 * | 9/2006 | Rabiei et al. | 424/57 |
| 2009/0311297 A1 * | 12/2009 | Hontsu et al. | 424/422 |
| 2010/0119564 A1 | 5/2010 | Kasuga et al. | |
| 2010/0256758 A1 * | 10/2010 | Gordon et al. | 623/16.11 |

OTHER PUBLICATIONS

Low, It-Meng, "Depth-Profiling of crystal structure, texture, and microhardness in a functionally graded tooth enamel", 2004, J. Am. Ceram. Soc., vol. 87, pp. 2125-2131.*

International Search Report issued Aug. 30, 2011 in International (PCT) Application No. PCT/JP2011/066955.

Y. Hashimoto et al., "Hito Kan'yokei Kansaibo to Hydroxyapatite Sheet o Kumiawaseta Shinki Kotsu Saisei Yudo Membrane no Kaihatus", Dai 7 Kai Japanese Association of Regenerative Dentistry Gakujutsu Taikai, Journal of the Japanese Association of Regenerative Dentistry, vol. 7, No. 1, p. 82, P06, 2009.

M. Toda et al., "Fabrication of a Novel Bioceramic Membrane for Guided Bone Regeneration", Journal of the Ceramic Society of Japan, vol. 114, No. 10, pp. 799-801, 2006.

S. Hontsu et al., "Dental Application of Flexible Apatite Sheet", Function & Materials, vol. 31, No. 5, pp. 63-68, Apr. 5, 2011.

S. Hontsu et al., "Flexible Apatite Sheet o Mochita Enamel-Shitsu no Kaishu Hozon", Dai 32 Kai The Annual Meeting of the Japanese Society for Biomaterials Yokoshu, p. 64, Nov. 29, 2010.

* cited by examiner

(a) Enamel
(b) HAp film

FIG. 3

(a) Dentin
(b) HAp film

HARD TISSUE REGENERATION MATERIAL AND HARD TISSUE REGENERATION METHOD

FIELD OF THE ART

The present invention relates to a hard tissue restoration material that is excellent in hard tissue restoration ability, protection properties, and aesthetic properties and to a hard tissue restoration method that uses the material.

BACKGROUND ART

Tissue repair using a bone graft material is performed on bone defects of long bones, cervical vertebrae, skull bones, etc. In regard to material quality, the bone graft material is required to have excellent biocompatibility and osteoconductive ability. A calcium phosphate-based ceramic, etc., such as hydroxyapatite (hereinafter abbreviated as "HAp"), etc., is often used as such a material. However, when such a ceramic is used in a form of a bulky, massive formed object, there is a problem that a central portion is high in probability of infection. A binder, such as gelatin, etc., is thus used (see, for example, Patent Document 1).

Also, tooth decay bacteria attaches to a dental surface to form plaque and the tooth decay bacteria, which thereby initiates dental caries, metabolizes foodstuffs inside the plaque to produce an acid that dissolves calcium and phosphorus immediately below the dental surface, thereby decalcifying dental enamel and forming an incipient caries state. As substances that promote recalcification, HAp and other calcium phosphate-based ceramics, etc., are known. However, HAp, etc., are poor in solubility in water and poor in adhesion to teeth, and thus a sufficient effect cannot be obtained by a means, such as coating, etc.

Therefore, for example, a dental adhesive film having HAp, etc., dispersed in a water-soluble or swelling supporting substance that adheres to teeth is used (see, for example, Patent Document 2) or electromagnetic waves are irradiated on a dental surface coated with a coating agent containing HAp to grow HAp crystals on the dental surface (see, for example, Patent Document 3).

However, with the films described in Patent Documents 1 and 2, fixing onto hard tissue is difficult to achieve because a fixing force of gelatin, etc., is not sufficient. Also the method of Patent Document 3 cannot be implemented easily because a coating agent irradiating apparatus is required.

Further, the conventionally available hard tissue restoration materials are mainly purported for hard tissue repair of a hard tissue defect, etc., and cannot restore tissue in a periphery of a bone or tooth, for example, periodontal tissue (alveolar bone, periodontal membrane, cementum, and gum) in a case of a tooth.

In addition, whitening, with which teeth are bleached by a bleaching chemical, such as hydrogen peroxide, urea peroxide, etc., is performed to make teeth appear white. However, there is a problem that surfaces of teeth that have been whitened by a bleaching chemical, such as hydrogen peroxide, urea peroxide, etc., become covered with pellicles and plaque in a short time and return of color occurs at an early stage.

On the other hand, the present inventors have already developed a biocompatible ceramic film having flexibility and pliability that is useable for tissue grafting, cell observation, etc., of skin, etc. (see Patent Document 4).

PRIOR ART DOCUMENTS

Patent Documents

Patent Document 1: Japanese Translation of International Application No. 2003-517326
Patent Document 2: Japanese Translation of International Application No. 2004-536032
Patent Document 3: Japanese Published Unexamined Patent Application No. Hei 10-337296
Patent Document 4: International Patent Publication No. 2007-108373

SUMMARY OF THE INVENTION

Problem to be Resolved by the Invention

An object of the present invention is to provide a hard tissue restoration material that is excellent in hard tissue restoration ability, extremely effective in promoting recalcification of dental enamel, and excellent in protection properties and aesthetic properties and a hard tissue restoration method that uses the material.

Means for Solving the Problem

The present inventors found that, by simply being put in contact with a tooth defect portion or a bone tissue defect portion, the present hard tissue restoration material adheres substantially irreversibly, protects the bone tissue defect portion, and exhibits excellent hard tissue restoration ability and have thereby come to complete the present invention. That is, the present invention provides the following.

A hard tissue restoration material according to the present invention is a biocompatible ceramic film with flexibility and pliability that is obtained by forming the biocompatible ceramic film on a substrate that includes a portion that is removable under an environment in which a shape of the biocompatible ceramic film can be maintained and thereafter removing the substrate, on which the biocompatible ceramic film has been formed, under that environment.

The hard tissue restoration material may be one that is formed by laminating a plurality of the biocompatible ceramic films. Also, the biocompatible ceramic film of the hard tissue restoration material may be a film of an apatite selected from the group consisting of HAp, fluoridated hydroxyapatite (hereinafter abbreviated as "FAp"), carbonate apatite, and element substituted apatite.

Further, an apatite precursor that contains $Ca^{2+}$ and $PO_4^{3-}$, such as monocalcium phosphate (hereinafter abbreviated as "MCPM"), dicalcium phosphate (hereinafter abbreviated as "DCPD"), tricalcium phosphate (hereinafter abbreviated as "α-TCP" or "β-TCP"), tetracalcium phosphate (hereinafter abbreviated as "TTCP"), octacalcium phosphate (hereinafter abbreviated as "OCP"), etc., may be laminated on the hard tissue restoration material.

The hard tissue restoration material is preferably a dental treatment material, a dental aesthetic material, a dental restorative/preservative material, or a bone filling material. As mentioned above, the hard tissue restoration material according to the present invention becomes fixed substantially irreversibly simply upon contact. Also, a color thereof is transparent to white. Also, the materials thereof are HAp, etc., which are safe. The material can thus be used not only as medical/dental material but also as a dental cosmetic material for aesthetic purposes. In particular, by bonding the hard tissue restoration material according to the present invention to a surface of a tooth immediately after whitening, return of color can be prevented and the tooth can be restored/preserved.

The hard tissue restoration method according to the present invention is a method of bonding or winding the hard tissue restoration material to or around a hard tissue defect site. Also, a plurality of the hard tissue restoration materials may be bonded to or wound around the hard tissue defect site. Also, the hard tissue restoration material, on which the apatite precursor, such as the α-TCP, etc., is laminated, may be used.

Effect(s) of the Invention

The hard tissue restoration material according to the present invention has flexibility and pliability and thus even with a bone tissue defect portion that is not planar, the hard tissue restoration material can be bonded to or wound around while being made to conform to the surface. Also, the hard tissue restoration material according to the present invention can be fixed substantially irreversibly simply by putting it in contact with the bone tissue defect portion and without requiring a special apparatus, etc.

Also, the hard tissue restoration material according to the present invention is transparent to white. The materials of the hard tissue restoration material according to the present invention are HAp, etc., which are safe. The material can thus be used not only as medical material but also as a dental cosmetic material for aesthetic purposes.

MODE(S) FOR CARRYING OUT THE INVENTION

1. Hard Tissue Restoration Material

A hard tissue restoration material according to the present invention can be manufactured, for example, by substantially the same method as a manufacturing method described in Patent Document 4. Specifically, the hard tissue restoration material can be manufactured by a manufacturing method that includes a plurality of steps, such as a film forming step, a removal step (dissolution step), etc. The details of these steps shall now be described.

(1) Film Forming Step

The film forming step is a step in which a biocompatible ceramic film is formed on a substrate that includes a portion that is removable under an environment in which a shape of the biocompatible ceramic film can be maintained.

1) Substrate

As the substrate used in this step, for example, that which is made of a material that includes a portion that dissolves in a solvent that does not dissolve the biocompatible ceramic film such as described in Patent Document 4 may be cited. Specifically, a water-soluble inorganic salt, such as sodium chloride, potassium chloride, or other halogenated alkali metal or amorphous magnesium oxide, etc., a water-soluble organic matter, such as crystals of an amino acid, such as glycine, etc., a molded object of a resin or wax, etc., that is soluble in an organic solvent, or an aromatic based material, such as naphthalene, etc., can be cited. Among these, a resin or a dental wax, etc., is preferable in enabling a large biocompatible ceramic film to be manufactured readily and being inexpensive.

Besides the above, for example, any material that can be removed under an environment in which the shape of the biocompatible ceramic film can be maintained, such as a resin that is decomposed by irradiation of ultraviolet rays or by heating, a material, which, like phosphorus or iodine, sublimes upon heating, a material, which, like wax, melts or combusts upon heating, etc., may be used without any restriction in particular as the substrate.

A shape of the substrate is not restricted in particular and may be plate-like, semispherical, tubular, or any other shape that is matched to a shape of the hard tissue restoration material to be manufactured. In particular, a crown shape or bridge shape, etc., that is matched to a shape of tooth crown to be treated is preferable.

Also, the substrate may be arranged from a plurality of different materials instead of from a single material. For example, instead of the substrate being made of just a material that dissolves in a solvent that does not dissolve the biocompatible ceramic, the substrate may include a portion made of a material that dissolves in the solvent and a portion made of a material, such as a glass plate, steel plate, etc., that does not dissolve in the solvent.

By using a substrate that partially uses a material that does not dissolve in the solvent, a need to re-prepare an entire substrate each time the biocompatible transparent ceramic film is to be manufactured is eliminated and the hard tissue restoration material can thereby be manufactured more inexpensively.

Also, by using a substrate in which projections, made of a material that dissolves in the solvent, are provided in a fixed pattern on an upper surface of a plate made of a material that does not dissolve in the solvent, a hard tissue restoration material with penetrating holes opened therein can be manufactured. For example, by manufacturing a hard tissue restoration material with penetrating holes at positions close to a defect site and bonding the material upon impregnating the penetrating holes with a pharmaceutical, etc., restoration of the hard tissue surface and treatment of a periphery of the hard tissue can be performed in parallel.

Such a substrate can be manufactured by performing on a glass plate or steel plate, etc., which does not dissolve in the solvent, coating of a material, which dissolves in the solvent, by using a laser ablation method, sputtering method, ion beam vapor deposition method, electron beam vapor deposition method, vacuum vapor deposition method, molecular beam epitaxy method, chemical vapor deposition method, etc., or spraying, by a spray, etc., of a liquid in which the material that dissolves in the solvent is dissolved followed by drying, etc.

2) Biocompatible Ceramic

The biocompatible ceramic refers to an apatite, a raw material thereof, or a mixture containing an apatite. Here, an apatite refers to a group of minerals with the composition $M_{10}(ZO_n)_6X_2$, where M signifies, for example, Ca, Na, Mg, Ba, K, Zn, or Al, $ZO_n$ signifies, for example, $PO_4$, $SO_4$, or $CO_3$, and X signifies, for example, OH, F, O, or $CO_3$. The apatite may, for example, be HAp, FAp, carbonate apatite, and an element substituted apatite. Among these, HAp, which is high in biocompatibility, and FAp, which is high in acid resistance and suited for dental applications, are more preferable. Also, as examples of raw materials (precursors) of apatite, apatite precursors containing $Ca^{2+}$ and $PO_4^{3-}$, such as MCPM, DCPD, α-TCP, β-TCP, TTCP, and OCP, can be cited, and as an example of a mixture that contains apatite, biological apatite (hereinafter abbreviated as "BAp") collected from a bone of a cow, etc., can be cited.

3) Film Forming

For film forming, any film forming method may be used without restriction as long as it is a method, for example, the laser ablation method, the sputtering method, ion beam vapor deposition method, electron beam vapor deposition method, vacuum vapor deposition method, molecular beam epitaxy method, chemical vapor deposition method, etc., that uses a known film forming apparatus. Among these, the laser ablation method is preferable in that a uniform film can be obtained with good efficiency.

The laser ablation method is performed, for example, according to the following procedure. First, the substrate is placed in a laser ablation apparatus, vacuum is drawn, and a water-vapor-containing gas or a carbon-dioxide-gas-containing gas is introduced into the apparatus. Then, a laser beam, generated from a laser light source that includes a laser generating apparatus, such as an ArF excimer laser generating apparatus, etc., a mirror, a lens, etc., is irradiated onto a target. The biocompatible ceramic making up the target is thereby decomposed to release atoms, ions, clusters, etc., and a target side of the substrate is coated by the biocompatible ceramic film.

Here, as the target, an object formed by processing and molding a powder of the biocompatible ceramic in a die is used. Also as the water-vapor-containing gas, water vapor, an oxygen-water vapor mixed gas, an argon-water vapor mixed gas, a helium-water vapor mixed gas, a nitrogen-water vapor mixed gas, or an air-water vapor mixed gas, etc., may be used alone or in combination, and as the carbon-dioxide-gas-containing gas, carbon dioxide gas, an oxygen-water vapor/carbon dioxide gas mixed gas, an argon-water vapor/carbon dioxide gas mixed gas, a helium-water vapor/carbon dioxide gas mixed gas, a nitrogen-water vapor/carbon dioxide gas mixed gas, or an air-water vapor/carbon dioxide gas mixed gas, etc., may be used alone or in combination.

In order for the biocompatible ceramic film to have flexibility and pliability and to maintain a fixed level of strength, a thickness of the biocompatible ceramic film is set to 1 to 100 μm and preferably 4 to 50 μm. A substrate temperature, a gas pressure of an atmosphere gas, etc., and other various conditions for forming the biocompatible ceramic film by the laser ablation method, etc., must thus be adjusted in consideration of the arrangement and characteristics of the laser ablation apparatus, etc., so as to fall within ranges corresponding to the thickness of the biocompatible ceramic film.

(2) Removal Step

The removal step is a step in which the biocompatible ceramic film is obtained by removing the substrate, under an environment in which the shape of the biocompatible ceramic film can be maintained, from the substrate with the biocompatible ceramic film formed thereon. As a specific example, a method of immersing the substrate with the biocompatible ceramic film formed thereon in a solvent as described in Patent Document 4 can be cited.

As the solvent to be used in this step, an aqueous solvent, organic solvent, polar solvent, non-polar solvent, etc., may be used without any restriction in particular as long as it is a liquid that does not dissolve the biocompatible ceramic film but dissolves at least a portion of the substrate that is in contact with the biocompatible ceramic film. In a case of an aqueous solvent, pure water, a buffer solution for cell culture, or a liquid medium for cell culture, etc., is more preferable. Also in a case of an organic solvent, acetone, hexane, or an alcohol, etc., that is volatile and does not remain on the bioceramic film is preferable. A dissolution time, solvent temperature, etc., may be adjusted as appropriate in accordance with the material, thickness, etc., of the substrate. Also, a plurality of solvents may be combined in accordance with the material of the substrate.

Also, in a case of using a substrate made of a material that decomposes, sublimes, melts, or combusts, etc., upon ultraviolet irradiation or heating, the substrate is removed using a known apparatus, such as an ultraviolet lamp, heating furnace, etc. A wavelength and intensity of the irradiated ultraviolet rays or a temperature, atmosphere, etc., during heating may be set in accordance with the material of the substrate within ranges in which the shape of the biocompatible ceramic film can be maintained.

After removal of the substrate, the biocompatible ceramic film may be dried (drying step) and may be heat-treated (heat treatment step).

(3) Drying Step

The drying step is a step in which the biocompatible ceramic film that has been isolated from the substrate by dissolution of the substrate is taken out of the solvent by forceps, etc., and air-dried or dried by an apparatus. Deformation and damaging of the obtained hard tissue restoration material can thereby be prevented.

(4) Heat Treatment Step

When a heat treatment step of performing heat treatment in a water-vapor-containing gas or a carbon-dioxide-gas-containing gas of a high temperature of 300 to 1200° C. is added after completion of film forming or after drying of the film to further crystallize the biocompatible ceramic film, a denser hard tissue restoration material can be obtained.

The hard tissue restoration material obtained as described above may be used with its shape being as it is or may be used upon cutting to a specific shape. By cutting to a specific shape, the material can be filled more densely in a hard tissue defect site.

Also, the hard tissue restoration material manufactured from HAp, FAp, carbonate apatite, or element substituted apatite has a property of adsorbing biologically-relevant molecules. Therefore various growth/differentiation factors, such as TGF-β (transforming growth factor), BMP (bone morphogenetic protein), IGF-1 (insulin-like growth factor 1), PDGF (platelet-derived growth factor), and bFGF (fibroblast growth factor), and other factors can be adsorbed onto the hard tissue restoration material. By bonding the hard tissue restoration material, with such various factors adsorbed thereon, to a tooth, restoration of a peripheral tissue of a bone or tooth is also made possible.

Further, the hard tissue restoration material obtained by the above steps is transparent. The hard tissue restoration material can be processed to be white in color by performing (1) heat treatment at a temperature of no less than 350° C. to increase crystallinity of the film, increase unevenness of the film surface, and thereby make the material reflect light diffusely, (2) hydrothermal treatment of the film to increase the unevenness of the film surface and thereby make the material reflect light diffusely, (3) coating of the film surface with nanoparticles of apatite to increase the unevenness of the film surface and thereby make the material reflect light diffusely, or (4) coating of the film with a white coating and further bonding of a film on an upper portion to make the material a sandwich type material, etc. The hard tissue restoration material can thereby be made excellent in aesthetic properties.

In addition, the hard tissue restoration material may be manufactured by performing film forming upon changing the target and overlapping different types of biocompatible ceramic films. Also, an apatite precursor containing $Ca^{2+}$ and $PO_4^{3-}$, such as MCPM, DCPD, α-TCP, β-TCP, TTCP, or OCP, etc., may be laminated on the biocompatible ceramic film by performing a known method, such as a powder deposition method, simulated body fluid method, alternate immersion method, molecular precursor method, etc., on the surface of the biocompatible ceramic film. Different properties, for example, both strength and adhesion to hard tissue can thereby be improved.

2. Adhesion Method

Figure 1:
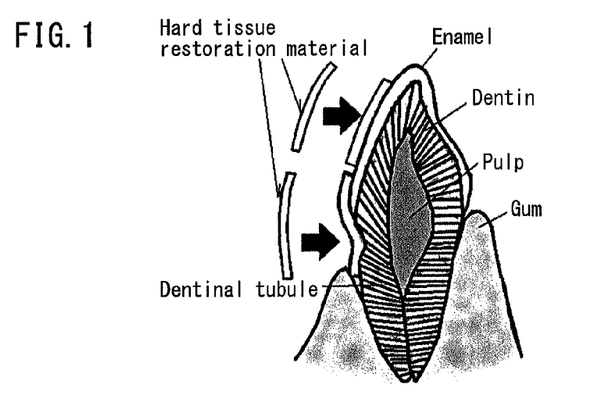
FIG. 1 is a schematic view of a method of using a hard tissue restoration material according to the present invention for restoration of an enamel of a tooth.

The hard tissue restoration material according to the present invention is adhered firmly to a hard tissue defect site by being bonded to or wounded around the site. The material adheres substantially irreversibly and can thus be adhered without an adhesive, etc. FIG. 1 is a schematic view of a method of using the hard tissue restoration material according to the present invention for restoration of an enamel of a tooth. As shown in FIG. 1, the hard tissue restoration material according to the present invention can be fixed by simply bonding it to a hard tissue defect site.

A reason for this is considered to be that when the HAp, etc., of the hard tissue restoration material and a surface of a tooth substance come in contact, attractive forces due to intermolecular forces act to produce a state in which fixing occurs readily. When large amounts of collagen and other organic matter and water are contained, the hard tissue restoration material according to the present invention does not become fixed readily and even after being fixed, stress is generated in the hard tissue restoration material according to the present invention due to contraction due to drying so that cracking and partial detachment occurs. Thus, in the process of fixing, organic matter present on surfaces of tooth substances (both enamel and dentin), etc., is removed by polishing, etc. or a water amount may be controlled.

The hard tissue restoration material according to the present invention may have a plurality of holes opened therein or a plurality of the materials may be used overlappingly. A bonding liquid used during bonding is thereby made more permeable and even in a case where a defect site is deep, sufficient filling can be achieved. In case where a plurality of the hard tissue restoration materials are used overlappingly, the hard tissue restoration materials of the same type may be overlapped or the hard tissue restoration materials of a plurality of types may be overlapped. For example, by overlapping a material that is low in crystallinity and close to being amorphous, a material that is low in crystallinity, and a material that is high in crystallinity in that order from a side close to the hard tissue, both a fixing property and strength can be realized at the same time.

Also, the following methods may be used to fix the hard tissue restoration material and the hard tissue even more firmly.

(1) Fixing Using a Decalcification/Recalcification Mode

The apatite film and a tooth substance may be fixed by attaching the hard tissue restoration material to a tooth substance using a weakly acidic solution containing $Ca^{2+}$ and $PO_4^{3-}$, such as artificial saliva or an aqueous monocalcium phosphate solution, to cause temporary decalcification to occur at an interface of the hard tissue restoration material and the tooth substance and thereafter causing recalcification to occur by returning the $Ca^{2+}$ and $PO_4^{3-}$ in supersaturated states to the tooth substance under a neutral or alkaline environment. Unlike in a case where a pharmaceutical or polymer material, etc., is used, a possibility of allergy is low and invasiveness can be lessened because only inorganic substances, such as apatite, calcium phosphate, etc., are used.

(2) Adhesion Using a Polymer Material

A tooth substance adhesion system based on a polymer that is currently used in dental treatment may be applied to fix the hard tissue restoration material and the tooth substance. The tooth substance adhesion system enables adhesion to be completed in a single step and in a short time.

(3) Fusion Using Melting of Apatite by a Laser

An output of a tooth substance removal laser used currently in dental treatment may be controlled to melt HAp and fuse the apatite film and the tooth substance. Unlike in the case where a pharmaceutical or polymer material, etc., is used, the possibility of allergy can be lessened because only inorganic substances, such as apatite, calcium phosphate, etc., are used.

By using the hard tissue restoration material according to the present invention, not only enamel but other hard tissues, including dentin, can also be restored. The hard tissue restoration material according to the present invention can thus be used as a dental treatment material, dental aesthetic material, or dental restorative/preservative material capable of restoration of fine unevenness of a tooth surface, protection, cavity prevention, tooth substance reinforcement, whitening action, treatment of hyperesthesia, etc., or as a medical material for treatment of a bone defect, fracture, etc.

Although the present invention shall now be described by way of examples, the present invention is by no means restricted to the examples.

EXAMPLE 1

1. Performance Test of Hard Tissue Restoration Material

The hard tissue restoration material according to the present invention was manufactured and states of fixing to tooth substances, etc., were examined. The details are described below.

(1) Manufacture of Hard Tissue Restoration Material

An HAp film was formed by the laser ablation (hereinafter abbreviated as "PLD") method on a substrate made of an NaCl monocrystal. Specifically, a sample holding apparatus of a PLD apparatus (designed by at Hontsu Laboratory, School Of Biology-Oriented Science And Technology, Kinki University; manufactured by Seinan Industries Co., Ltd.) was made to hold a sodium chloride crystal (10 mm×10 mm×2.5 mm) and an HAp film of approximately 10 μm thickness was formed by performing PLD using an ArF excimer laser ($\lambda$=193 nm, pulse width=20 ns) for 18 hours.

The substrate temperature was 300° C., the atmosphere gas used was an oxygen-water vapor mixed gas, and a gas pressure of the mixed gas was 0.8 mTorr. A Cell yard pellet (made by Pentax, stoichiometric composition: HAp) was used as the target to be the raw material of the film.

The NaCl substrate was then dissolved in pure water and a transparent and flexible HAp film with dimensions of 10 mm×10 mm and a film thickness of 12 μm was recovered. Thereafter, heat treatment at 400° C. under an oxygen-water vapor atmosphere was performed for 10 hours to crystallize the HAp film.

(2) Evaluation Experiment of Enamel Recalcification Ability

Figure 2:
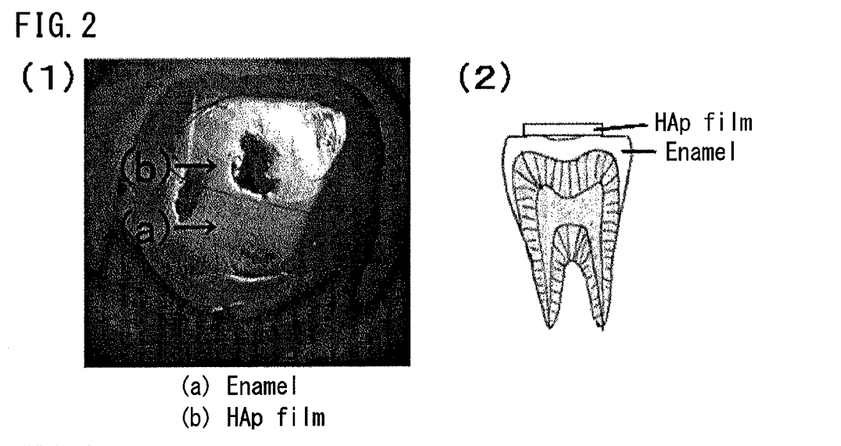
FIG. 2 is a photograph taken using an optical microscope to check fixing circumstances of an HAp film on an enamel after 90 days.

Extracted human teeth were cut at root/crown boundary portions and after exposing the enamel and dentin, respectively, the crown portions were polished by a waterproof abrasive paper #600 and subject to the experiment. As shown in FIG. 2 (2) and FIG. 3(2), the HAp films that were respectively cut to dimensions of 5 mm×5 mm were placed on respective sample central portions of the enamel and the dentin and artificial saliva (Saliveht, made by Teijin Pharma) was sprayed thereon. Thereafter, the artificial saliva was sprayed every three days and serial observations were made for 90 days (n=3). After 90 days, circumstances of fixing of the HAp film onto the tooth substance were checked using an optical microscope. Also, each of the enamel and dentin samples was enveloped in resin, sectioned longitudinally with a low-speed diamond saw so as to pass through a central portion of the HAp-film-fixed portion, and upon treatment by a conventional method, an interface of the fixed portion was checked using a scanning electron microscope. The extracted human teeth were used in the experiments after receiving the approval of the Ethics Committee of Osaka Dental University doctors.

(3) Results of Observation of the Fixed States by the Optical Microscope

FIG. 2(1) is a photograph taken using the optical microscope to check the fixing circumstances of the HAp film on the enamel after 90 days. In the figure, (a) indicates a portion at which the HAp film was not fixed and (b) indicates a portion at which the HAp film was fixed. From the figure, a polishing scar could be observed at the portion at which the HAp film was not fixed and a polishing scar could not be observed at the portion at which the HAp film was fixed. It was thereby found that the enamel can be restored/protected by using the hard tissue restoration material according to the present invention.

Figure 3:
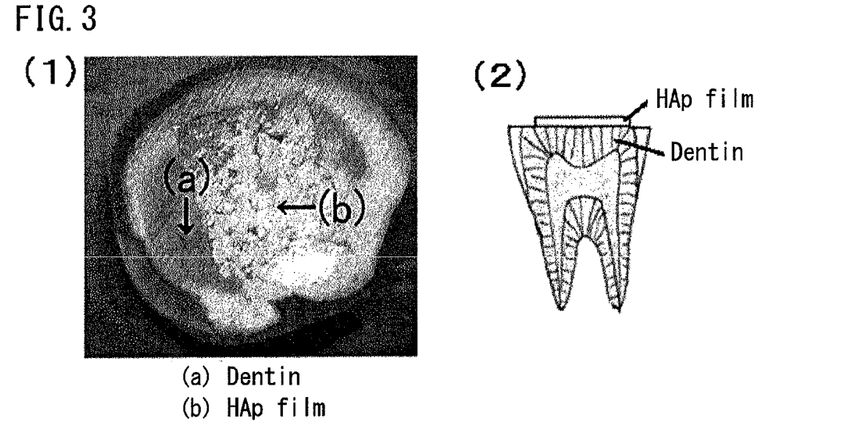
FIG. 3 is a photograph taken using an optical microscope to check fixing circumstances of an HAp film on a dentin after 90 days.

FIG. 3(1) is a photograph taken using the optical microscope to check the fixing circumstances of the HAp film on the dentin after 90 days. In the figure, (a) indicates a portion at which the HAp film was not fixed and (b) indicates a portion at which the HAp film was fixed. From the figure, although cracking, etc., could not be observed at the portion at which the HAp film was not fixed and cracking or partial detachment of the film was observed at the portion at which the HAp film was fixed, a large portion of the film was fixed firmly. The cracking occurred due to the sample drying process for electron microscope observation because the dentin contains 30% organic matter and water. It was thereby found that the dentin can be restored/protected by using the hard tissue restoration material according to the present invention.

Figure 4A:
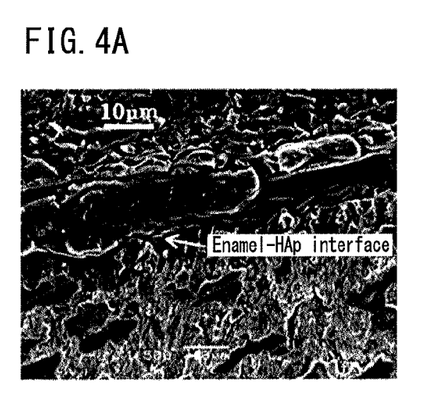
FIG. 4A and FIG. 4B show photographs taken using a scanning electron microscope to check fixing circumstances of the HAp film on the enamel after 90 days.
Figure 4B:
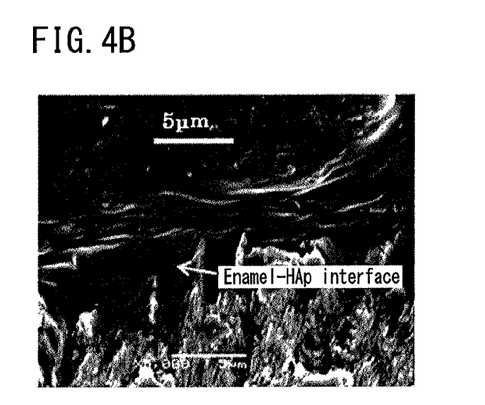

(4) Results of Observation of the Fixed States by the Scanning Electron Microscope FIG. 4A and FIG. 4B show photographs taken using the scanning electron microscope to check the fixing circumstances of the HAp film on the enamel after 90 days. As indicated by dimension bars in the figures, FIG. 4A is a weakly magnified photograph (1,500 times) and FIG. 4B is a strongly magnified photograph (5,000 times). From FIG. 4A, an image in which a non-structured film of approximately 10 μm thickness is fixed to the enamel surface could be observed. Portions at which the film is fixed in conformance to the unevenness of the enamel surface were also seen in the strongly magnified image of FIG. 4B.

Figure 5A:
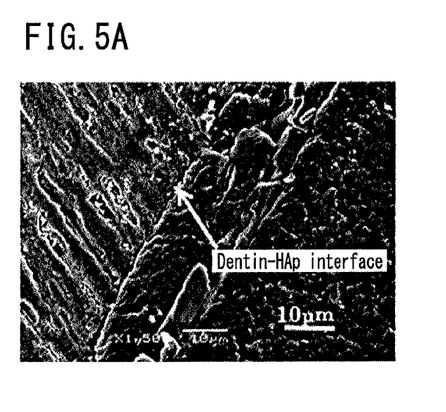
FIG. 5A and FIG. 5B show photographs taken using a scanning electron microscope to check fixing circumstances of the HAp film on the dentin after 90 days.
Figure 5B:
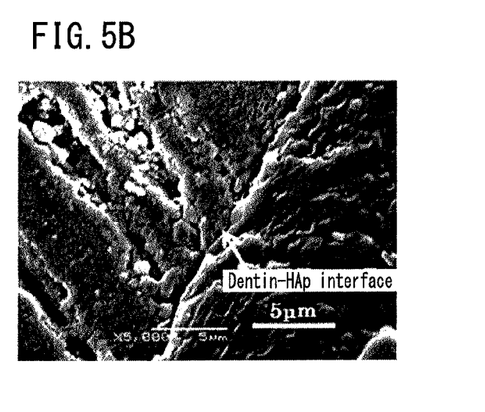

FIG. 5A and FIG. 5B show photographs taken using the scanning electron microscope to check fixing circumstances of the HAp film on the dentin after 90 days. As indicated by dimension bars in the figures, FIG. 5A is a weakly magnified photograph (1,500 times) and FIG. 5B is a strongly magnified photograph (5,000 times). From FIG. 5A, an image in which a non-structured film of approximately 10 μm thickness is fixed to the dentin surface in the same manner as on the enamel surface could be observed. Portions at which the film is fixed so as to fill the dentinal tubules in the dentin surface were also seen in the strongly magnified image of FIG. 5B.

From this example, it was found that the hard tissue restoration material according to the present invention can restore both enamel and dentin by being bonded to surfaces of the enamel and dentin.

EXAMPLE 2

2. Whitening of BAp Film

After manufacturing a film made of BAp, whitening of the BAp film by heat treatment was examined. The details are described below.

(1) Manufacture of BAp Film

BAp powder (made by Eccera Co., Ltd.) was press-molded and used as a bulk target. The ArF excimer laser ($\lambda$=193 nm, pulse width=20 ns) was irradiated onto this target for 6 hours to form a BAp film of 4μ thickness on a nNaCl substrate (10×10×3 mm) by the PLD method. Thereafter, just the NaCl substrate was dissolved by immersion in pure water and a transparent and flexible BAp film with dimensions of 10 mm×10 mm and a film thickness of 4 μm was recovered.

The substrate temperature was room temperature, the atmosphere gas used was an oxygen-water vapor mixed gas, and a gas pressure of the mixed gas was 0.8 mTorr. The same PLD apparatus as that used in Example 1 was used.

(2) Heat Treatment

Figure 6:
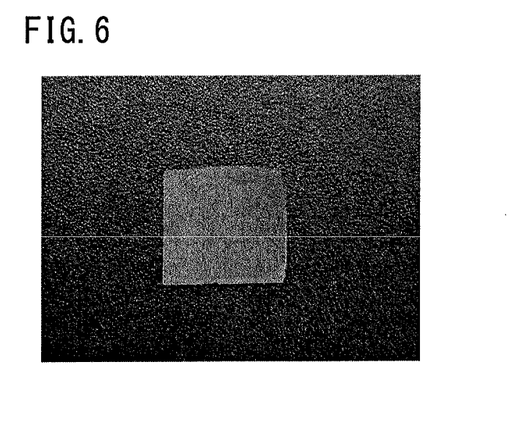
FIG. 6 is an optical photograph of an outer appearance of a crystallized BAp film.
Figure 7:
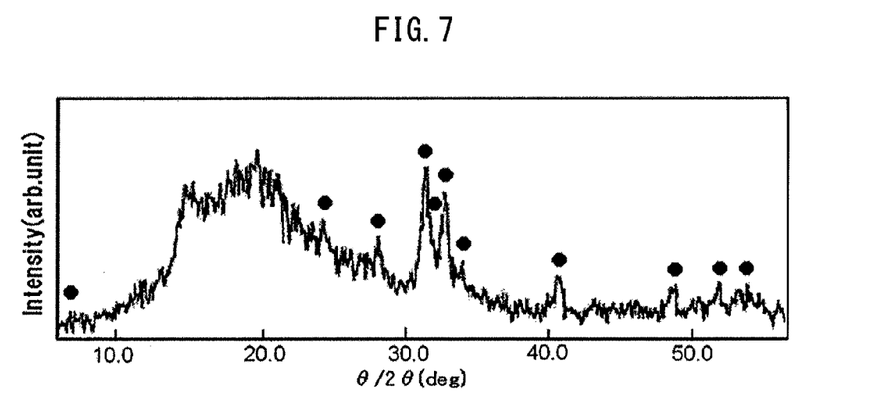
FIG. 7 is an X-ray diffraction (hereinafter abbreviated as "XRD") pattern of the crystallized BAp film.

The film was post-annealed and crystallized under conditions of heating to 350° C. for 15 hours in carbon dioxide gas. FIG. 6 is a photograph of an outer appearance of the crystallized BAp film obtained. FIG. 7 is a diagram of an XRD pattern of the crystallized BAp film obtained. In FIG. 7, a broad peak near 20° of the XRD is the peak of an amorphous $SiO_2$ fixing plate on which the film was fixed during measurement. From FIG. 6, it was confirmed that whitening of the crystallized BAp film obtained was achieved. Also, from the XRD peak marked with the black circle in FIG. 7, it was confirmed that the BAp film is crystallized. From the above, it was found that the BAp film can be whitened by crystallization.

EXAMPLE 3

3. Manufacture of FAp Film

FAp is known to be stable and improved in acid resistance in comparison to HAp. An FAp film was thus manufactured and its properties were examined.

(1) Manufacture of Hard Tissue Restoration Material

FAp powder (made by Taihei Chemical Industrial Co., Ltd.) was press-molded and used as a bulk target. The ArF excimer laser ($\lambda$=193 nm, pulse width=20 ns) was irradiated onto this target for 8 hours to deposit 4 μm of an FAp film on an NaCl substrate (10×10×3 mm) by the PLD method.

The substrate temperature was 300° C., the atmosphere gas used was an oxygen-water vapor mixed gas, and a gas pressure of the mixed gas was 0.8 mTorr. The same PLD apparatus as that used in Example 1 was used.

Figure 8:
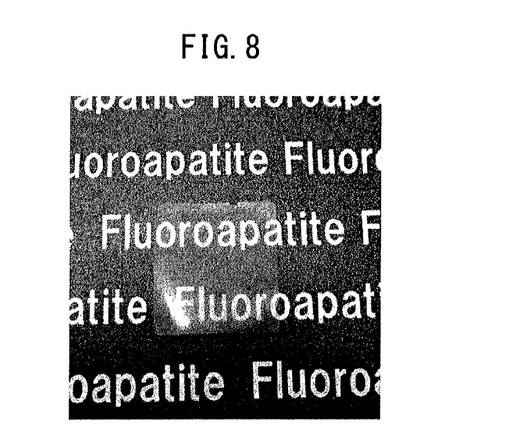
FIG. 8 is an optical photograph of an outer appearance of a crystallized FAp film.

Just the NaCl substrate was then dissolved in pure water and a transparent and flexible FAp film with dimensions of 10 mm×10 mm and a film thickness of 4 μm was recovered. Thereafter, heat treatment in air at 450° C. for 10 hours was performed to crystallize the FAp film. FIG. 8 is a photograph of an outer appearance of the crystallized FAp film obtained. From the figure, it was confirmed that a hard tissue restoration material made of a transparent crystallized FAp film was successfully obtained.

(2) Evaluation of the FAp Hard Tissue Restoration Material

Figure 9A:
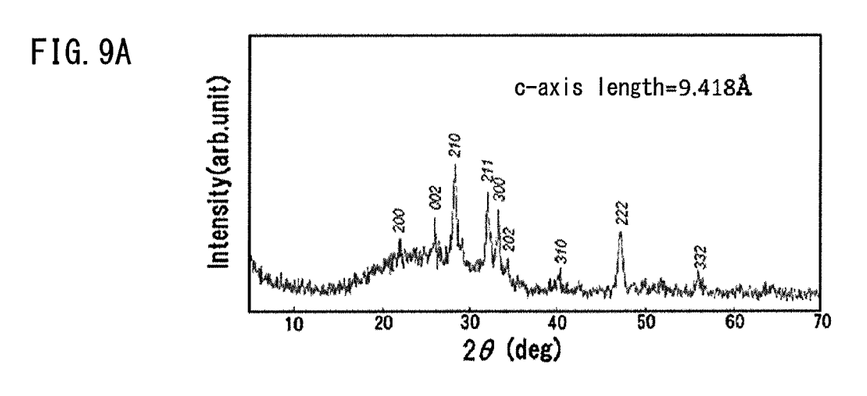
FIG. 9A is an XRD pattern of the crystallized FAp film. Also.
Figure 9B:
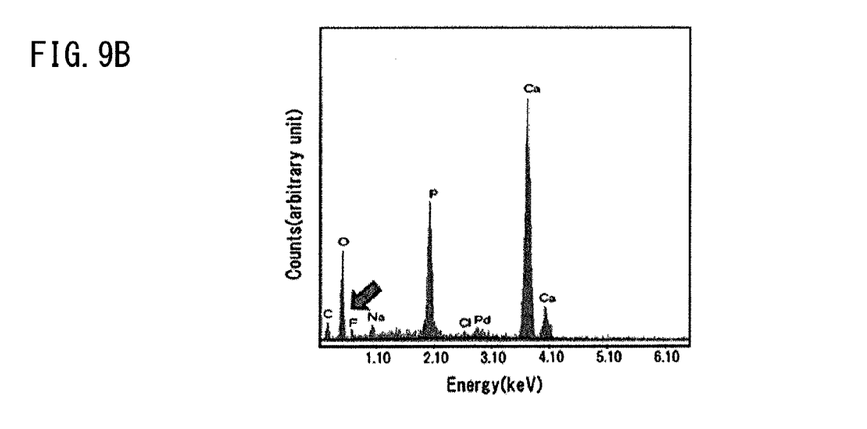
FIG. 9B shows results of energy dispersive X-ray analysis (EDX) of the crystallized FAp film. Further.
Figure 9C:
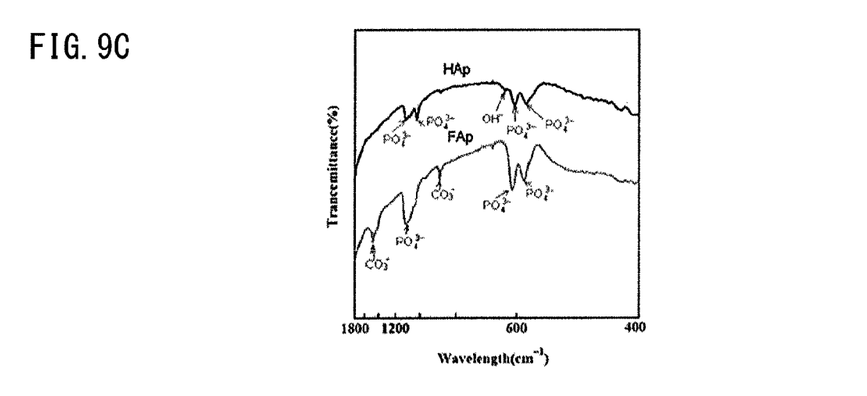
FIG. 9C shows results of analysis and comparison of the crystallized FAp film and the crystallized HAp film by Fourier transform infrared spectroscopic analysis.

An XRD of the crystallized FAp film was measured by XRD based on a 2θ/θ method. The results are shown in FIG. 9A. From the figure, it was found that the crystallized FAp film is crystallized. Also, the crystallized FAp film was analyzed by energy dispersive X-ray analysis (EDX). The results are shown in FIG. 9B. From this figure, the presence of fluorine in the FAp film was confirmed. Further, the crystallized FAp film and the HAp film were analyzed by Fourier transform infrared spectroscopic analysis (FT-IR) and the analysis results were compared. The results are shown in FIG. 9C. From this figure, it was found that in comparison to the HAp film, the hydroxyl group peak is reduced in the FAp film and thus that the hydroxyl group in the HAp film is substituted by fluorine in the FAp film. It was thereby confirmed that an FAp film was obtained.

EXAMPLE 4

Figure 10:
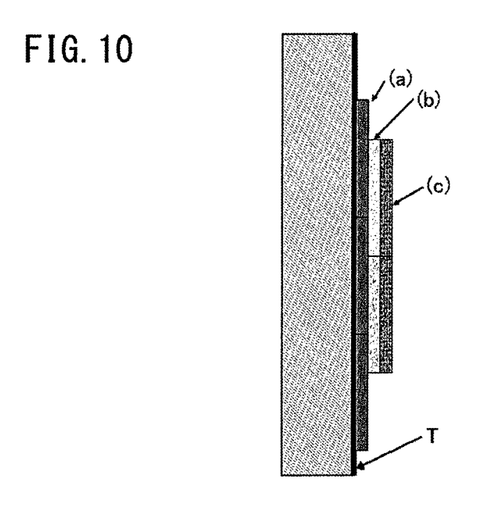
FIG. 10 is a schematic view of a method of overlappingly bonding hard tissue restoration materials of different properties onto a hard tissue.

4. Confirmation of Effects of Overlappingly Bonding Hard Tissue Restoration Materials The effects of improvement of fixing strength by overlappingly bonding hard tissue restoration materials of different properties onto a hard tissue were examined. Specifically, the examination was performed as follows. First, as shown in FIG. 10, the three types of hard tissue restoration materials of (a) a film that is low in crystallinity, close to being amorphous, and readily dissolved, (b) a film that is low in crystallinity, and (c) a film that is high in crystallinity and difficult to dissolve were manufactured in order of bonding onto a tooth substance T. The crystallinities of the hard tissue restoration materials manufactured and influences on fixing strength of overlappingly bonding these materials onto the tooth substance were examined.

(1) Hard Tissue Restoration Materials

HAp films were manufactured by the PLD method in the same manner as in Example 1. The HAp films were respectively (a) left as it is without heat treatment, (b) heat treated at 350° C. for 2 hours under an oxygen-water vapor atmosphere, and (c) heat treated at 350° C. for 10 hours under an oxygen-water vapor atmosphere.

(2) Crystallinity Analysis

Figure 11A:
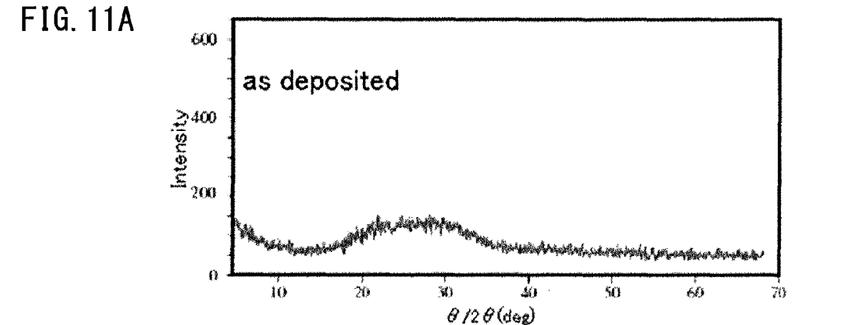
FIG. 11A, FIG. 11B and FIG. 11C show XRD patterns of the respective hard tissue restoration materials of FIG. 10.
Figure 11B:
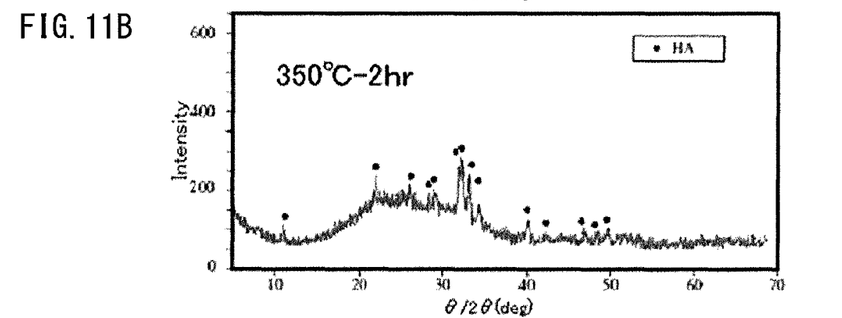
Figure 11C:
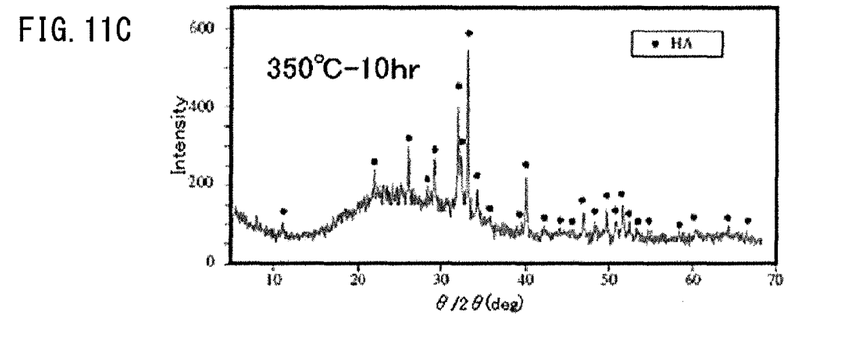

XRD patterns of the hard tissue restoration materials (a) to (c) were measured by the 2θ/θ method. The results are shown in FIG. 11A, FIG. 11B and FIG. 11C. From these figures, it was found that the hard tissue restoration materials (a) to (c) differ in crystallinity due to differences in heat treatment.

(3) Tensile Test

Figure 12:
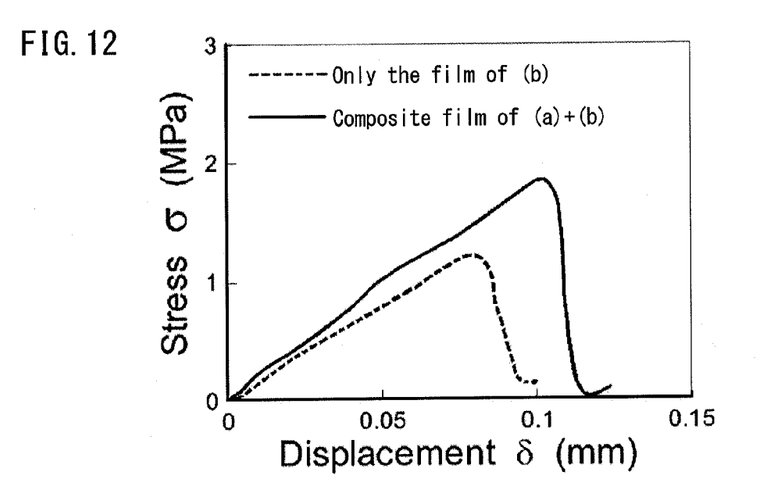
FIG. 12 is a diagram of results of examining, by a tensile test, an influence of overlappingly bonding the respective hard tissue restoration materials of FIG. 10 on a fixing strength of the hard tissue restoration materials on an enamel.

The influences of overlappingly bonding films of different crystallinities on the fixing strength between the hard tissue restoration materials and the tooth substance were examined. Specifically, the hard tissue restoration materials were bonded onto enamel in the same manner as in Example 1 and the fixing strength between the hard tissue restoration materials and the enamel was measured and comparatively examined 72 hours after bonding. The results are shown in FIG. 12. From this figure, it was found that the fixing strength of the hard tissue restoration materials with respect to the tooth substance is improved by bonding overlappingly.

EXAMPLE 5

5. Confirmation of Effects Due to Lamination

Influences of lamination of α-TCP, which is an apatite precursor, on a surface of a hard tissue restoration material on the fixing time and fixing strength of the hard tissue restoration material and enamel were examined.

(1) Manufacture of Hard Tissue Restoration Material with α-TCP Laminated

A powder of α-TCP (made by Taihei Chemical Industrial Co., Ltd.) was press-molded and used as a bulk target. The ArF excimer laser ($\lambda$=193 nm, pulse width=20 ns) was irradiated onto this bulk target for 1 hour to laminate an α-TCP thin film of 300 nm thickness by the PLD method on the hard tissue restoration material manufactured in the same manner as in Example 1. The substrate temperature was room temperature, the atmosphere gas used was oxygen gas, and a gas pressure of the gas was 0.8 mTorr. Also, the same PLD apparatus as that used in Example 1 was used. Further, for comparison, the hard tissue restoration material without the α-TCP laminated was prepared separately.

(2) Comparison of Fixing Performance by X-Rays

Figure 13A:
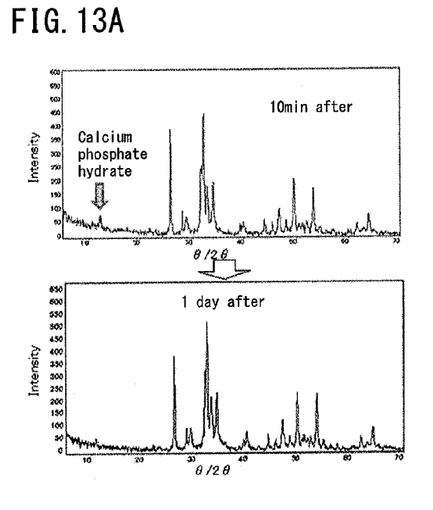
FIG. 13A and FIG. 13B show XRD patterns of results of examining an influence of presence/non-presence of a laminated layer of α-TCP on a fixing time of a hard tissue restoration material on an enamel.
Figure 13B:
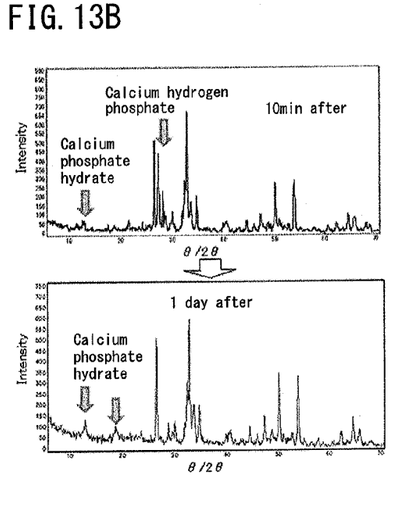

After respectively placing the hard tissue restoration material with the α-TCP, which is an apatite precursor, laminated and the hard tissue restoration material without the α-TCP laminated on extracted human teeth with the enamel exposed in the same manner as in Example 1, the films were bonded using an aqueous monocalcium phosphate solution of pH 5.5. Artificial saliva was coated on every day after bonding. Also, the XRD pattern by the 2θ/θ method was measured 10 minutes after and 1 day after. The results are shown in FIG. 13A and FIG. 13B. FIG. 13A is a diagram showing changes of the XRD pattern of the hard tissue restoration material with the α-TCP laminated and FIG. 13B is a diagram showing changes of the XRD pattern of the hard tissue restoration material without the α-TCP laminated.

From FIG. 13A, it was confirmed that a peak of calcium phosphate hydrate, which is an apatite precursor, in the XRD pattern of the hard tissue restoration material with the α-TCP laminated decreases and the XRD pattern becomes the same as that of the enamel after 1 day from bonding onto the enamel. On the other hand, from FIG. 13B, it was confirmed that in the XRD pattern of the hard tissue restoration material without the α-TCP laminated, an apatite precursor peak is seen besides the XRD pattern of the enamel and matching with the peaks of the enamel does not occur even after 1 day from bonding onto the enamel. Although not illustrated, it was separately confirmed that it takes approximately 1 week for the XRD pattern of the hard tissue restoration material without the α-TCP laminated to become equivalent to the XRD pattern of the enamel. From these results, it was found that by laminating the α-TCP film, which is an apatite precursor, onto the hard tissue restoration material, the fixing time of the hard tissue restoration material and the enamel can be shortened.

(3) Tensile Test

Figure 14:
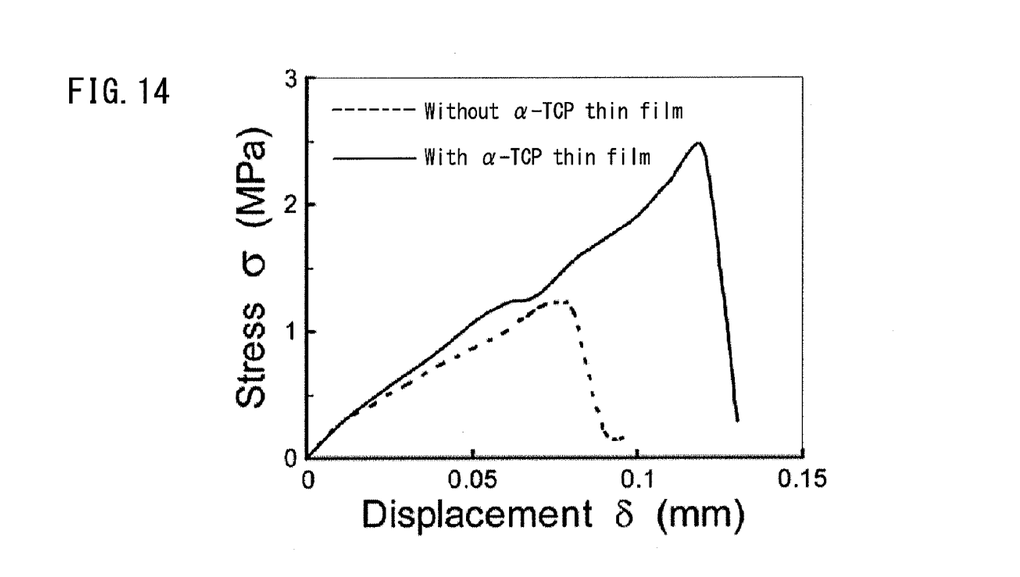
FIG. 14 is a diagram of results of examining, by the tensile test, influences of presence/non-presence of the laminated layer of α-TCP on the fixing strength of the hard tissue restoration material on the enamel.

Influences of the presence/non-presence of the α-TCP thin film that is an apatite precursor on the fixing strength between the hard tissue restoration material and a tooth substance were examined. Specifically, each hard tissue restoration material was bonded to enamel in the same manner as in (2), and a fixing strength between each hard tissue restoration material and the enamel was measured and comparatively examined 72 hours after the bonding. The results are shown in FIG. 14. From the figure, it was found that the fixing strength of the hard tissue restoration material with respect to the tooth substance is improved by providing the α-TCP thin film on the hard tissue restoration material.

(4) Scratch Test

Influences of the presence/non-presence of the α-TCP thin film that is an apatite precursor on the fixing characteristics between the hard tissue restoration material and a tooth substance were examined. Specifically, bonding of the hard tissue restoration materials to enamel was performed in the same manner as in (2), and a scratch test by a scratch tester was performed 1 day after and 3 days after in the case of the hard tissue restoration material with the α-TCP laminated and performed 3 days after and 10 days after in the case of the hard tissue restoration material without the α-TCP laminated, the circumstances of fixing between the hard tissue restoration material and the enamel were observed and comparatively examined from the scratch powder. The results are shown in FIG. 15A, FIG. 15B, FIG. 15C, FIG. 16A and FIG. 16B.

Figure 15A:
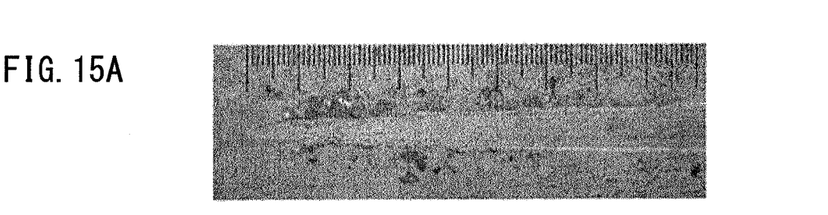
FIG. 15A, FIG. 15B and FIG. 15C show photomicrographs of results of a scratch test in a case of using a hard tissue restoration material in which an α-TCP thin film is laminated.
Figure 15B:
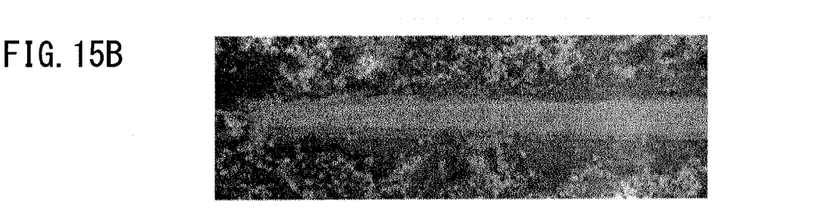
Figure 15C:
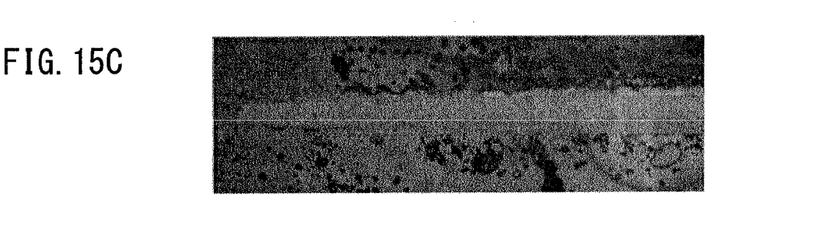

The result of the scratch test in the case of just the enamel is shown in FIG. 15A, that of 1 day after using the hard tissue restoration material with the α-TCP thin film laminated is shown in FIG. 15B, and that of 3 days after using the hard tissue restoration material with the α-TCP thin film laminated is shown in FIG. 15C. Also, the result of the scratch test of 3 days after using the hard tissue restoration material without the α-TCP thin film laminated is shown in FIG. 16A, and that of 10 days after using the hard tissue restoration material without the α-TCP thin film laminated is shown in FIG. 16B.

From FIGS. 15B and 15C, it could be confirmed that in the case of use of the hard tissue restoration material with the α-TCP thin film laminated, the scratch powder resulting from the scratching on the 1st day was uniform such that a boundary between the hard tissue restoration material and the enamel could not be discerned and the hard tissue restoration material and the enamel were integrated.

Figure 16A:
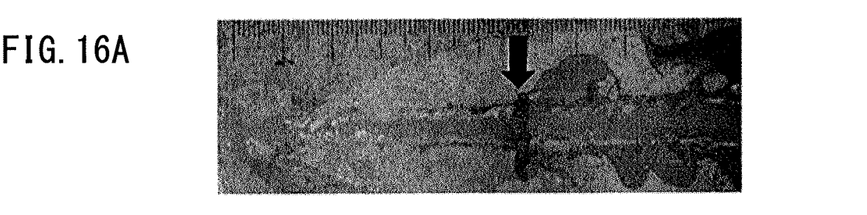
FIG. 16A and FIG. 16B show photomicrographs of results of a scratch test in a case of using a hard tissue restoration material in which an α-TCP thin film is not laminated.
Figure 16B:
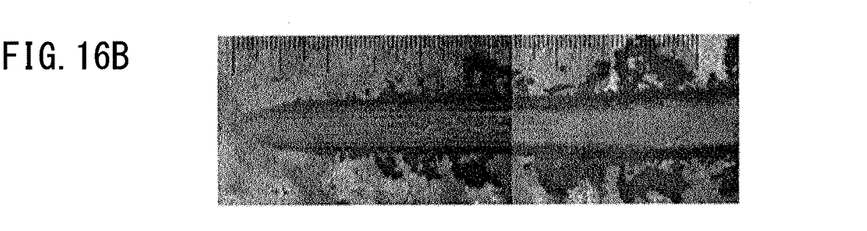

On the other hand, from FIG. 16A, peeling powder resulting from peeling of the hard tissue restoration material from the enamel is seen at a boundary portion (indicated by an arrow) between the hard tissue restoration material and the enamel after 3 days and it could thus be confirmed that the hard tissue restoration material and the enamel are not integrated. Also, from FIG. 16B, it could be confirmed that after 10 days, the scratch powder became uniform such that a boundary between the hard tissue restoration material and the enamel could not be discerned and the hard tissue restoration material and the enamel were thus integrated.

From these results, it was found that by providing the α-TCP thin film on the hard tissue restoration material, integration of the hard tissue restoration material and the enamel occurs in approximately 1 day.

INDUSTRIAL APPLICABILITY

The hard tissue restoration material according to the present invention becomes fixed to enamel, without any special treatment as long as a liquid, such as saliva, etc., is present, and can protect the tooth substance. The hard tissue restoration material can thus be directly bonded onto an affected tooth in an incipient stage of caries or of a hyperesthetic patient to promote recalcification of the enamel and thereby perform fundamental treatment. In comparison to conventional treatment methods for hyperesthesia, etc., there is no need to scrape the enamel of the tooth matrix, etc., and thus low invasiveness and reduction of treatment period can be anticipated. Further, the treatment promotes the restoration of autologous tissue without the use of drugs and thus a burden on a patient can be lightened significantly. Also, the hard tissue restoration material according to the present invention is transparent or white. A whitening effect can thus be anticipated. Further, the hard tissue restoration material according to the present invention also provides an action of protection of the tooth surface. The hard tissue restoration material according to the present invention is thus effective as a dental treatment material, a dental aesthetic material, or a dental restorative/preservative material. Further, the material can be fixed to enamel and to dentin and is thus effective for use as a bone filling material for treating bone defects and as a medical treatment material for treating a fracture, etc.

What is claimed is:

1. A hard tissue restoration material consisting of
   a first biocompatible ceramic film,
   a second biocompatible ceramic film having a higher crystallinity than the first biocompatible ceramic film,
   a third biocompatible ceramic film having a higher crystallinity than the second biocompatible ceramic film, and
   optionally, α-tricalcium phosphate laminated on the surface of the material,
   wherein the hard tissue restoration material is flexible, pliable and capable of being wound around a hard tissue, and
   wherein the second biocompatible ceramic film is located between the first biocompatible ceramic film and the third biocompatible ceramic film to form a layered structure.

2. The hard tissue restoration material according to claim 1, wherein at least one of the biocompatible ceramic films is a film of an apatite selected from the group consisting of hydroxyapatite, fluoridated hydroxyapatite, carbonate apatite, and element substituted apatite.

3. The hard tissue restoration material according to claim 1, wherein the hard tissue restoration material is a dental treatment material, a dental aesthetic material, a dental restorative/preservative material, or a bone filling material.

4. The hard tissue restoration material of claim 1, wherein the hard tissue restoration material is subjected to heat treatment at no less than 350° C. for 2-15 hours and diffusely reflects light.

5. The hard tissue restoration material of claim 1, wherein the hard tissue restoration material has a thickness of 1 to 100 μm.

6. The hard tissue restoration material of claim 1, wherein the hard tissue restoration material has a thickness of 4 to 50 μm.

7. The hard tissue restoration material of claim 1, wherein each of the biocompatible ceramic films is formed by a process comprising depositing biocompatible ceramic on a substrate by laser ablation followed by removal of each biocompatible ceramic film from the substrate.

8. A method of restoring hard tissue comprising bonding or winding the hard tissue restoration material according to claim 1 to or around a hard tissue defect site.

9. The method according to claim 8, wherein a plurality of the hard tissue restoration materials are overlappingly bonded to or wound around the hard tissue defect site.

10. The method according to claim 8, wherein the hard tissue restoration material is formed by laminating an apatite precursor on a surface.

11. The method according to claim 10, wherein the apatite precursor is any one of monocalcium phosphate, dicalcium phosphate, tricalcium phosphate, tetracalcium phosphate, and octacalcium phosphate.

* * * * *